US006855509B2

(12) United States Patent
Dai et al.

(10) Patent No.: US 6,855,509 B2
(45) Date of Patent: Feb. 15, 2005

(54) PROTEIN S FUNCTIONAL ASSAY AND KIT THEREFOR

(75) Inventors: Yong Dai, Wappingers Falls, NY (US); Biqing Ye, Dumont, NJ (US); Kui Chen, Chatham, NJ (US); Pau Bruguera, Barcelona (ES); Daniel E. Lawson, Nanuet, NY (US); ShaMay Tang, Bardonia, NY (US)

(73) Assignee: Instrumentation Laboratory Company, Lexington, MA (US)

( * ) Notice: Subject to any disclaimer, the term of this patent is extended or adjusted under 35 U.S.C. 154(b) by 151 days.

(21) Appl. No.: 10/029,406

(22) Filed: Dec. 19, 2001

(65) Prior Publication Data

US 2003/0073070 A1 Apr. 17, 2003

Related U.S. Application Data

(60) Provisional application No. 60/256,703, filed on Dec. 19, 2000.

(51) Int. Cl.$^7$ ................................................. C12Q 1/56
(52) U.S. Cl. ........................................................ 435/13
(58) Field of Search ............................................ 435/13

(56) References Cited

U.S. PATENT DOCUMENTS

| | | | |
|---|---|---|---|
| 4,622,389 A | 11/1986 | Nagasawa et al. | 530/331 |
| 4,692,406 A | 9/1987 | Becker et al. | 435/13 |
| 4,755,461 A | 7/1988 | Lawson et al. | 435/13 |
| 4,849,403 A | 7/1989 | Stocker et al. | 514/2 |
| 5,001,069 A | 3/1991 | Bartl et al. | 436/86 |
| 5,051,357 A | 9/1991 | Hassouna | 435/13 |
| 5,059,525 A | 10/1991 | Bartl et al. | 435/13 |
| 5,147,805 A | 9/1992 | Preda et al. | 436/86 |
| 5,169,786 A | 12/1992 | Carroll et al. | 436/69 |
| 5,187,067 A | 2/1993 | Koike et al. | 435/7.9 |
| 5,200,322 A | 4/1993 | Matsumoto | 435/13 |
| 5,223,427 A | 6/1993 | Edgington et al. | 435/240.27 |
| 5,254,350 A | 10/1993 | Barrow et al. | 424/570 |
| 5,270,451 A | 12/1993 | Hawkins et al. | 530/381 |
| 5,308,756 A | 5/1994 | van de Waart et al. | 435/13 |
| 5,314,695 A | 5/1994 | Brown | 424/450 |
| 5,358,853 A | 10/1994 | Butler et al. | 435/13 |
| 5,374,617 A | 12/1994 | Morrissey et al. | 514/8 |
| 5,391,380 A | 2/1995 | Barrow et al. | 424/570 |
| 5,418,141 A | 5/1995 | Zweig et al. | 435/13 |
| 5,426,031 A | 6/1995 | Hawkins et al. | 435/13 |
| 5,439,802 A | 8/1995 | Rosén | 435/13 |
| 5,443,960 A | 8/1995 | Dahlbäck | 435/13 |
| 5,472,850 A | 12/1995 | Morrissey | 435/13 |
| 5,502,651 A | 3/1996 | Jackson et al. | 364/509 |
| 5,504,064 A | 4/1996 | Morrissey et al. | 514/8 |
| 5,504,067 A | 4/1996 | Morrissey et al. | 514/8 |
| 5,506,112 A | 4/1996 | Lang et al. | 435/13 |
| 5,508,170 A | 4/1996 | Butler et al. | 435/13 |
| 5,525,478 A | 6/1996 | Matschiner | 435/13 |
| 5,643,739 A | 7/1997 | Varadi et al. | 435/13 |
| 5,705,395 A | 1/1998 | Griffin et al. | 436/69 |
| 5,716,795 A | 2/1998 | Matschiner | 435/13 |
| 5,726,028 A | 3/1998 | Kraus | 435/13 |
| 5,753,510 A | 5/1998 | Kraus | 436/16 |
| 5,766,869 A | 6/1998 | Arkel et al. | 435/13 |
| 5,780,255 A | 7/1998 | Preda | 435/23 |
| 5,834,223 A | 11/1998 | Griffin et al. | 435/13 |
| 5,858,724 A | 1/1999 | Novy, Jr. et al. | 435/69.6 |
| 5,874,256 A | 2/1999 | Bertina et al. | 435/69.6 |
| 6,040,147 A | 3/2000 | Ridker et al. | 435/7.24 |
| 6,083,757 A | 7/2000 | Griffin et al. | 436/69 |
| 6,090,570 A | 7/2000 | Kraus | 435/13 |
| 6,100,072 A | 8/2000 | Brucato et al. | 435/69.7 |
| 6,203,816 B1 | 3/2001 | Brown | 424/450 |
| 6,211,344 B1 | 4/2001 | Kraus et al. | 530/413 |

FOREIGN PATENT DOCUMENTS

| | | |
|---|---|---|
| CA | 2037434 | 9/1991 |
| EP | A 0 229 234 | 7/1987 |
| EP | 0 406 971 A1 | 1/1991 |
| EP | 0 445 626 A2 | 9/1991 |
| EP | 286323 | 12/1993 |
| EP | 434377 | 8/1995 |
| EP | 0 696 642 A1 | 2/1996 |
| WO | 88/07543 | 10/1988 |
| WO | 90/11368 | 10/1990 |
| WO | 91/01382 | 2/1991 |
| WO | 91/01383 | 2/1991 |
| WO | 91/02812 | 3/1991 |
| WO | 92/08479 | 5/1992 |
| WO | 93/07492 | 4/1993 |
| WO | 93/10261 | 5/1993 |
| WO | 93/13211 | 7/1993 |
| WO | 93/23074 | 11/1993 |

OTHER PUBLICATIONS

Madden et al., "Recombinant human protein C: comparative functional studies with human plasma protein C", Trhombosis Research 57 (3) : 425–35 (1990).*

Almasy et al. "Linkage of the Factor V Gene with Protein C and Protein S Levels Not Due to the Factor V Leiden Mutation", *Washington*, p. 387, (1999).

Amer et al. "Impairment of the Protein C Anticoagulant Pathway in a Patient with Systemic Lupus Erythematosus, Anticardiolipin Antibodies and Thrombosis," *Thrombosis Research*, 57:247–258 (1990).

Amiral et al. "New Direct Assay of Free Protein S Antigen Using Two Distinct Monoclonal Antibodies Specific for the Free Form," *Blood Coag. and Fibrin.*, 5:179–186 (1994).

(List continued on next page.)

*Primary Examiner*—Sandra Saucier
(74) *Attorney, Agent, or Firm*—Testa, Hurwitz & Thibeault, LLP

(57) ABSTRACT

The invention relates generally to a new functional protein S assay and kit that is based on the ability of endogenous protein S to prolong clotting time. In the assay procedure, a test plasma sample is diluted with protein S deficient plasma, followed by the addition of purified or recombinant tissue factor (pTF or rTF), purified natural or synthetic phospholipid (pPL or sPL) and activated protein C (APC) or protein C activator (PCA). The clotting time is then measured and compared to a standard curve or a normal control.

26 Claims, 1 Drawing Sheet

OTHER PUBLICATIONS

Andrews et al. "Conservation of Tissue Factor Primary Sequence Among Three Mammalian Species," *Gene*, 98:265–269 (1991).

Bader et al. "Multicentric Evaluation of a New PT Reagent Based on Recombinant Human Tissue Factor and Synthetic Phospholipids," *Thromb. Haemost.*, 71(3):292–299 (1994).

Baele et al. "Comparison of a Recombinant Thromboplastin with Thrombotest™ for Oral Anticoagulant Control," *Haemost.*, 26:11–15 (1996).

Bauer. "Hypercoaguability–A New Cofactor in the Protein C Anticoagulant Pathway," *New England Journal of Medicine*, 330:566–567 (1994).

Beauchamp at al. "High Prevalence of a Mutation in the Factor V Gene Within the U.K. Population: Relationship to Activated Protein C Resistance and Familial Thrombosis," *British J. of Haemost.*, 88:219–222 (1994).

Bertina et al. "Mutation in Blood Coagulation Factor V Associated with Resistance to Activated Protein C," *Nature*, 369:64–67 (1994).

Boyer–Neumann et al. "Comparison of Functional Assays for Protein S: European Collaborative Study of Patients with Congenital and Acquired Deficiency," *Thomb. and Haemost.*, 70(6):946–950 (1993).

Blangero et al. "Normal Activated Protein C Response has a Large Genetic Component," *Florencia*, PS.920, p. 226, (Jun. 9, 1997).

Blangero et al. "Genetic Factors Influence Quantitative Variation in Tissue Factor Pathway Inhibitor," *Florencia*, PS–1666, p. 409, (1997).

Blombäck et al. "Chromogenic Peptide Substrates in the Laboratory.Diagnosis of Clotting Disorders," *Haemostasis and Thrombosis*, Bloom and Thomas (eds.), $2^{nd}$ ed, 967–981 (1987).

Cattaneo. "Hyperhomocysteinemia, Atherosclerosis and Thrombosis," *Thromb. Haemost.*, 81:165–176 (1999).

Chromogenix, Coatest APC Resistance Kit Instructions, May 1993.

Chromogenix, Coatest APC Resistance Kit Brochure, Jun. 1993.

Comp. "Laboratory Evaluation of Protein S Status," *Seminars in Thromb. and Haemost.*, 16(2)177–181 (1990).

Cornillon et al. "Rat Coagulation Factor V Purification and Production of the Monospecific Antiserum," *Comp. Biochem. Physiol.*, 83B, 2: 397–401 (1986).

Cripe et al. "Structure of the Gene for Human Coagulation Factor V," *Biochemistry*, 31: 3777–3785 (1992).

Dahlbäck et al. "Resistance to Activated Protein C, the FV:$Q^{506}$ Allele, and Venous Thrombosis," *Ann. Hematol.*, 72:166–176 (1996).

Dahlbäck, "New Molecular Insights into the Genetics of Thrombophilia. Resistance to Activated Protein C Caused by $Arg^{506}$ to Gln Mutation in Factor V as a Pathogenic Risk Factor for Venous Thrombosis," *Thromb. Haemost.*, 74(1):139–148 (1995).

Dahlbäck. "Factor V Gene Mutation Causing Inherited Resistance to Activated Protein C as a Basis for Venous Thromboembolism," *J. Intern. Med.*, 237:221–227 (1995).

Dahlbäck et al. "Inherited Resistance to Activated Protein C is Corrected by Anticoagulant Cofactor Activity Found to be a Property of Factor V," *Proc. Natl. Acad. Sci.* (*USA*), 91:1396–1400 (1994).

Dahlbäck. "A New Model for Coagulation Factor V Suggesting a Unique Mechanism of Activation," *Scand. J. Clin. Lab. Invest.*, 48, Suppl.191:47–61 (1988).

Dahlbäck. "Factor VIII Defect Associated with Familial Thrombophilia," *Thrombosis & Haemostatis*, 65, Abstract 39:658 (1991).

Dahlbäck et al. "Familial Thrombophilia Due to a Previously Unrecognized Mechanism Characterized by Poor Anticoagulant Response to Activated Protein C: Prediction of a Cofactor to Activated Protein C," *Proc. Natl. Acad. Sci. USA*, 90:1004–1008 (1993).

Dahlbäck. "Thrombophilia: The Discovery of Activated Protein C Resistance," *Advances in Genetics: Incorporating Molecular Genetic Medicine*, Academic Press, (Hall et al. eds.), 135–175 (1995).

Dahlbäck et al. "A Natural Anticoagulant Pathway: Proteins C, S, C4b–Binding Protein an Thrombomodulin," *Haemostasis and Thrombosis* (Bloom et al. eds.), $3^{rd}$ edition, Churchill Livingstone, 671–698 (1994).

Dahlbäck. "The Protein C Anticoagulant System: Inherited Defects as Basis for Venous Thrombosis," *Thrombosis Research*, 77:1–43 (1995).

D'Angelo. "7 Prothrombin Time Standardization: The Problem of the Control Plasma," *Eur. J. Clin. Chem. Clin. Biochem.*, 33(12):1019–1022 (1995).

Denson et al. "Validity of the INR System for Patients with Liver Impairment," *Thromb. Haemost.*, 73(1):162 (1995).

DiScipio et al. "A Comparison of Human Prothrombin, Factor IX (Christmas Factor), Factor X (Stuart Factor), and Protein S," *Biochem.*, 16:698–704 (1977).

Duchemin et al. "A New Assay Based on Thrombin Generation Inhibition to Detect Both Protein C and Protein S Deficiencies in Plasma," *Thomb. and Haemost.*, 71(3):331–338 (1994).

Edson et al. "Laboratory Diagnosis of Inherited Protein S Deficiency," *Am. J. Clin. Pathol.*, 94(2):176–186 (1990).

Esmon. "The Roles of Protein C and Thrombomodulin in the Regulation of Blood Coagulation," *J. Biol. Chem.*, 264(9):4743–4746 (1989).

Esmon. "The Regulation of Natural Anticoagulant Pathways," *Science*, 235:1348–1352 (1987).

Esmon. "Protein C: Biochemistry, Physiology, and Clinical Implications," *Blood*, 62:1155–1158 (1983).

Faioni et al. "Another Protein S Functional Assay is Sensitive to Resistance to Activated Protein C," *Thomb. and Haemost.*, 72(4):648 (1994).

Faioni et al. "Resistance to Activated Protein C in Nine Thrombophilic Families: Interference in a Protein S Functional Assay," *Thromb. and Haemost.*, 70(6):1067–1071 (1993).

Falkon et al. "Tissue Factor Pathway Inhibitor and Anti–FXa Kinetic Profiles of a New Low–Molecular–Mass Heparin, Bemiparin, at Therapeutic Subcutaneous Doses," *Blood Coag. and Fibrin.*, 9:137–141 (1998).

Folsom et al. "Prospective Study of Hemostatic Factors and Incidence of Coronary Heart Disease," *Circulation*, 96(4):1102–1108 (1997).

Forastiero et al. "Evaluation of Recently Described Tests for Detection of the Lupus Anticoagulant," *Thromb. Haemost.*, 72(5):728–733 (1994).

Gari et al. "The Influence of Low Protein S Plasma Levels in Young Women, on the Definition of Normal Range," *Thromb. Res.*, 73(2):149–152 (1994).

Giddings et al. "Chapter 12: Laboratory Support in the Diagnosis of Coagulation Disorders," *Clinics in Haematology*, 14(2):571–595 (1985).

Griffin et al. "Anticoagulant Protein C Pathway Defective in Majority of Thrombophilic Patients," *Blood*, 82(7):1989–1993 (1993).

Griffin et al. "Activated Protein C Resistance: Molecular Mechanisms," *Thromb. Haemost.*, 74(1) 444–448 (1995).

Halbmayer et al. "The Prevalence of Poor Anticoagulant Response to Activated Protein C (APC Resistance) Among Patients Suffering from Stroke or Venous Thrombosis and Among Healthy Subjects,"*Blood Coag. and Fibrin.*, 5:51–57 (1994).

Han et al. "A Simple Functional Protein S Assay Using PROTAC®," *Clin. Lab. Haemat.*, 12:201–208 (1990).

Hemker et al. "Proteins Induced by Vitamin K Absence (PIVKAs) Effect of Coumarins on Circulating Clotting Factors," *Oral Anticoagulants*, Poller and Hirsch, eds., Arnold Press, London, 65–75 (1996).

Henkens et al. "Plasma Levels of Protein S, Protein C, and Factor X: Effects of Sex, Hormonal State and Age," *Thromb. Haemost.*, 74(5):1271–1275 (1995).

Hochuli et al. "Genetic Approach to Facilitate Purification of Recombinant Proteins with a Novel Metal Chelate Adsorbent," *Bio/Technology*, 1321–1325 (1988).

Kalafatis et al. "Role of the Membrane in the Inactivation of Factor Va by Activated Protein C," *J. Biol. Chem.*, 268(36):27246–27257 (1993).

Kalaftis et al. "Proteolytic Events That Regulate Factor V Activity in Whole Plasma from Normal and Activated Protein C (APC)-Resistant Individuals During Clotting: An Insight into the APC-Resistance Assay," *Blood*, 87(11): 4695–4707 (1996).

Kamiya et al. "Inherited Deficiency of Protein S in a Japanese Family with Recurrent Venous Thrombosis: A Study of Three Generations," *Blood*, 67 (2): 406–410 (1986).

Kamphuisen et al. "High Levels of Factor VIII Antigen are an Important Risk Factor of Deep–Vein Thrombosis," *Thrombosis—Acquired Risk Factors*, Abstract 1768, p. 398a.

Kane et al. "Blood Coagulation Factors V and VIII: Structural and Functional Similarities and TheIr Relationship to Hemorrhagic and Thrombotic Disorders," *Blood*, 71(3):539–555 (1988).

Kapur et al. "Factor V Inhibitor in Thrombosis," *American Journal of Hematology*, 42: 384–388 (1993).

Katzrnann. "Isolation of Functional Human Coagulation Factor V by Using a Hybridoma Antibody," *Proc. Natl. Acad. Sci. USA*, 78(1):162–166 (1981).

Kisiel. "Human Plasma Protein C: Isolation, Characterization and Mechanism of Activation by Alpha Thrombin," *J. Clin. Invest.*, 64:761–789 (1979).

Kisiel et al. "Anticoagulant Properties of Bovine Plasma Protein C Following Activation By Thrombin," *Biochem.*, 16(26):5824–5830 (1977).

Kisiel et al. "Proteolytic Activation of Protein C from Bovine Plasma," *Biochem.*, 15(22):4893–4900 (1976).

Kitchen et al. "Two Recombinant Tissue Factor Reagents Compared to Conventional Thromboplastins for Determination of International Normalised Ratio: A Thirty-Three-Laboratory Collaborative Study," *Thrornb. and Haemost.*, 76(3):372–376 (1996).

Kluft et al. "Effect of OraI Contraceptives on Haemostasis Variables," *Thromb. Haemost.*, 78(1):315–326 (1997).

Kobayashi et al. "Functional Activity of Protein S Determined with Use of Protein C Activated by Venom Activator," *Clin. Chem.*, 35(8):1644–1648 (1989).

Kolde. "Standardization of the Prothrombin Time: Clinical Results with a Recombinant Tissue Factor Reagent," *Haematologica*, 80 (supp to No. 2):7–13 (1995).

Koster et al. "Factor VII and Fibrinogen Levels as Risk Factors for Venous Thrombosis—A Case–Control Study of Plasma Levels and DNA Polymorphisms—The Leiden Thrombophilia Study (LETS)," *Thromb. Haemost.*, 71(6):719–722 (1994).

Koster et al. "Role of Clotting Factor VIII in Effect of von Willebrand Factor on Occurrence of Deep–Vein Thrombosis," *The Lancet*, 345:152–155 (1995).

Koster et al. "Venous Thrombosis Due to Poor Anticoagulant Response to Activated Protein C: Leiden Thrombophilia Study," *The Lancet*, 342:1503–1506 (1993).

Kovacs et al. "Assessment of the Validity of the INR System for Patients with Liver Impairment," *Thromb Haemost.*, 71(6):727–730 (1994).

Laudano et al. "Synthetic Peptides Modeled on Fibrin Polymerization Sites," *Ann NY Acad. Sci.* 408:315–329 (1983).

Laudano et al. "Studies on Synthetic Peptides that Bind to Fibrinogen and Prevent Fibrin Polymerization. Structural Requirements, Number of Binding Sites, and Species Differences," *Biochemistry*, 19:1013–1019 (1980).

Laudano et al. "Synthetic Peptide Derivatives that Bind to Fibrinogen and Prevent the Polymerization of Fibrin Monomers," *Proc. Natl. Acad. Sci. (USA)*, 75(7):3085–3089 (1978).

Lindblad et al. "Arterial and Venous Thromboembolism with Fatal Outcome and Resistance to Activated Protein C," *The Lancet*, 343(8902):917 (1994).

Maccaferri et al. "Protein S Activity in Patients with Heredofamilial Protein S Deficiency and in Patients with Juvenile Venous Thrombosis. Results of a Functional Method," *Thromb. Res.*, 64:647–658 (1991).

MacCallum et al. "Clotting Factor VIII and Risk of Deep–Vein Thrombosis," *The Lancet*, 345:804 (1995).

Majerus. "Bad Blood by Mutation," *Nature*, 369:14–15 (1994).

Mann. "Biochemistry and Physiology of Blood Coagulation," *Thromb. Haemost.*, 82(2):165–174 (1999).

Martinoli et al. "Fast Functional Protein C Assay Using Protac, A Novel Protein C Activator," *Thrombosis Research*, 43:253–264 (1986).

Marciniak. "Coagulation Inhibitor Elicited by Thrombin," *Science*, 170:452–453 (1970).

McAlpine et al. "A Pstl Polymorphism in the Human Coagulation Factor V (F5) Gene," *Nucleic Acids Research*, 18(24):7471 (1990).

Meijers et al. "High Levels of Coagulation Factor XI as a Risk Factor for Venous Thrombosis," *J. Med.*, 342(10):696–701 (2000).

Miletich et al. "Absence of Thrombosis in Subjects with Heterozygous Protein C Deficiency," *New Eng. J. Med.*, 317:991–996 (1987).

Mitchell et al. "A Fatal Thrombotic Disorder Associated with an Acquired Inhibitor of Protein C," *New Eng. J. Med.*, 317:1638–42 (1987).

Moraes et al. "Detection of Protein S Deficiency: A New Functional Assay Compared to an Antigenic Technique," *Pathology*, 32:94–97 (2000).

Murakami et al. The Level of Tissue Type–Plasminogen Activator and the Rate of Plasma Clot Lysis In Vitro, *Thromb. and Haemost.*, 65: Abstract 658:884 (1991).

Nilsson. "Assessment of Blood Coagulation and General Haemostasis," *Haemostasis and Thrombosis*, Bloom and Thomas (eds.), $2^{nd}$ ed, 922–932 (1987).

O'Brien et al. "Evaluation of Protein C and Protein S Levels During Oral Anticoagulant Therapy," *Clin. Lab. Haem.*, 20:245–252 (1998).

O'Donnell et al. "High Prevalence of Elevated Factor VIII Levels in Patients Referred for Thrombophilia Screening: Role of Increased Synthesis and Relationship to the Acute Phase Reaction," *Thromb. Haemost.*, 77(5):825–828 (1997).

Oger et al. "Assessment of Activated Protein C Resistance Using a New and Rapid Venom–Based Test: STA Staclot APC–R," *Blood Coagulation and Fibrinolysls*, 9:355–359 (1998).

Pel–Freez Biologicals. "Pel–Freez Molecular Diagnostics, Recombinant Rabbit Tissue Factor," *Pel–Freez Biologicals*, 1–5 (1997).

Poort et al. "A Common Genetic Variation in the 3'—Untranslated Region of the Prothrombin Gene is Associated with Elevated Plasma Prothrombin Levels and an Increase in Venous Thrombosis," *Blood*, 88(10):3698–3703 (1996).

Pratt et al. "Protein C lnhibitor Purification and Proteinase Reactivity," *Thrombos. Res.* 53:595–602 (1989).

Preda et al. "A Prothrombin Time–Based Functional Assay of Protein S," *Thromb. Res.*, 60:19–32 (1990).

Redondo et al. "Coagulation Factors II, V, VII, and X, Prothrombin Gene 20210G→A Transition, and Factor V Leiden in Coronary Artery Disease—High Factor V Clotting Activity is an Independent Risk Factor for Myocardial Infarction," *Arterioscler. Thromb. Vasc. Biol.*, 19:1020–1025 (1999).

Root–Bernstein et al. "Fibrinopeptide A Binds Gly–Pro–Arg–Pro," *Proc. Natl. Acad. Sci. (USA)*, 81:4339–4342 (1984).

Rosén et al. "Multicenter Evaluation of a Kit for Activated Protein C Resistance on Various Coagulation Instruments Using Plasmas from Healthy Individuals," *Thromb. and Haemost.*, 72(2):255–260 (1994).

Roussi et at. "French Multicentric Evaluation of Recombinant Tissue Factor (Recombiplastin) for Determination of Prothrombin Time," *Thromb. Haem.*, 72(5):698–704 (1994).

Salem et al. "Human Coagulation Factor $V_a$ is a Cofactor for the Activation of Protein C," *Proc. Nat. Acad. Sci. USA*, 80:1584–1588 (1983).

Seegers et al. "Relationship of 'New' Vitamin K–Dependent Protein C and "Old" Autoprothrombin Il–A," *Thromb. Res.*, 8:543–552 (1976).

Shen et al. "The Serine Protease Cofactor Factor V is Synthesized by Lymphocytes[1]," *The Journal of Immunology*, 150(7): 2992–3001 (1993).

Shen et al. "Factor V and Protein S as Synergistic Cofactors to Activated Protein C in Degradation of Factor VIIIa," *J. Biol. Chem.*, 269(29): 18735–18738 (1994).

Simioni et al. "A Protein S Functional Assay Yields Unsatisfactory Results in Patients with Activated Protein C Resistance," *Blood Coag. and Fibrin.*, 6:286–287 (1995).

Solymoss et al. "Kinetics of Inactivation of Membrane–bound Factor Va by Activated Protein C, Protein S Modulates Factor Xa Protection," *J. Biol. Chem.*, 263(29):14884–14890 (1988).

Soria et al. "Linkage Analysis Demonstrates that the Prothrombin G20210A Mutation Jointly Influences Plasma Prothrombin Levels and Risk of Thrombosis," *Blood*, 95(9):2780–2785 (2000).

Souto et al. "Genetic Determinants of Hemostasis Phenotypes in Spanish Families," *Circulation*, 101:1546–1551 (2000).

Souto et al. "Genetic Susceptibility to Thrombosis and Its Relationship to Physiological Risk Factors: The GAIT Study," *Am. J. Hum. Genet.*, 67:1452–1459 (2000).

Souto et al. "Genetics of Homocysteine and the Vitamins Involved in its Metabolism: Results from the Gait Project," *Washington*, 708:543 (1999).

Souto et al. "Genetlc Determinants of Venous Thrombosis and Their Relationship with Physiological Risk Factors: Results from the Gait Project," *Washington*, 2176:689 (1999).

Stenflo. "Structure and Function of Protein C," *Semin. Thromb. Haemost.*, 10(27):109–121 (1984).

Sun et al. "Blood Coagulation Factor Va Abnormality Associated with Resistance to Activated Protein C in Venous Thrombophilia," *Blood*, 83(11): 3120–3125 (1994).

Suzuki et al. "Inactivation of Human Coagulation Factor V by Activated Protein C," *J. Biol. Chem.*, 258(3):1914–1920 (1983).

Suzuki. "Gene Structure of Human Thrombomodulin, a Thrombin Receptor on Endothelium Acting as a Cofactor for Thrombin–Catalyzed Activation of Protein C," *Acta Haematol. Jon.*, 51(8):1655–1664 (1988).

Svensson et al. "Resistance to Activated Protein C as a Basis for Venous Thrombosis," *N.E. J. of Med.*, 330:517–522 (1994).

Takahashi et al. "Fast Functional Assay of Protein C in Whole Plasma Using a Snake Venom Activator Evaluation in Patients with Congenital and Acquired Protein C Deficiencies," *Clinica Chimica Acta*, 175:217–225 (1988).

Thompson et al. "Hemostatic Factors and the Risk of Myocardial Infarction or Sudden Death in Patients with Angina Pectoris," *N.E. J. Med.*, 332(10):635–641 (1995).

Thorelli et al. "The C–Terminal Region of the Factor V B–Domain is Crucial for the Anticoagulant Activity of Factor V," *J. Biol. Chem.*, 273(26):16140–16145 (1998).

Tripodi et al. "Recombinant Tissue Factor as Substitute for Conventional Thromboplastin in the Prothrombin Time Test," *Thromb. Haemost.*, 67(1):42–45 (1992).

Tuddenham. "Thombophilia: A New Factor Emerges from the Mists," *The Lancet*, 342:1501–1502 (1993).

van Dreden et al. "Discrimination of APC–R with a New One Step Procedure Using Factor V Deficient Plasma: STA–Staclot APC–R," *XVIIth 15$^{TH}$ Congress in Washington Diagnost. Stago.* (1999).

van Hylckama Vlieg et al. "High Levels of Factor IX Increase the Risk of Venous Thrombosis," *Blood*, 95(12):3678–3682 (2000).

van 't Veer et al. "Regulation of Prothrombinase Activity by Protein S," *Thromb. Haemost.*, 82:80–87 (1999).

van Wijnen et al. "A Plasma Coagulation Assay for an Activated Protein C–Independent Anticoagulant Activity of Protein S," *Thromb. Haemost.*, 80:930–935 (1998).

Vasse et al. "Protein C: Rouen, A New Hereditary Protein C Abnormality with Low Antiocoagulant But Normal Amidolytic Activities," *Thrombosis Research*, 56:387–398 (1989).

Voet et al. "Biochemistry," *John Wiley & Sons, Inc.* (eds.) 1086–1095 (1990).

Voorberg et al. "Association of Idiopathic Venous Thromboembolism with Single Point–Mutation at Arg$^{506}$ of Factor V," *The Lancet*, 343:1535–1536 (1994).

Vukovich et al. "Replacement Therapy for a Homozygous Protein C Deficiency–State Using a Concentrate of Human Protein C and S," *Br. J. Haematology*, 70:435–440 (1988).

Walker et al. "Regulation of Blood Coagulation by the Protein C System," *FASEB J.*, 6:2561–2567 (1992).

Walker et al. "Inactivation of Factor VIII by Activated Protein C and Protein S," *Arch. Biochem. Biophys.*, (1987).

Wolf et al. "A New Functional Assay for Human Protein S Activity Using Activated Factor V as Substrate," *Thromb. and Haemost.*, 62(4)1144–1145 (1989).

Woodhams et al. "Functional Protein S Assay Shows Improved Correlation with Clinical Symptoms in Hereditary Deficiency," *Thromb. Res.*, 57:651–657 (1990).

Zoller et al. "Linkage Between Inherited Resistance to Activated Protein C and Factor V Gene Mutation in Venous Thrombosis," *The Lancet*, 343:1536–1538 (1994).

Beck et al. (1988), "Protein C: ein Inhibitor der Blutgerinnung," *Diagnose & Labor*, 38:35–42 (Abstract in English).

Bertina (1990), "Specificity of Protein C and Protein S Assays," *Res. Clin. Lab.*, 20:127–138.

Bertina et al. (1985), "Determination of Plasma Protein S—The Protein Cofactor of Activated Protein C," *Thrombosis Haemostasis*, 268–272.

"Correlation of the APC Ratio with Free Protein S Antigen and with Protein C Activity" Appendix 5, 3 pages (Publication date not known).

Dade Behring Marburg GmbH (2000), "Pathromitin®," 1 page (Partial English translation provided).

Deutsche Norm, DIN 58 911 (1988), "Kalibrierung ven Gerinnugngszeit–MeBverfahren," 3 pages (English translation provided).

Deutsche Norm DIN 58 939 (1987), "Refererzplasma," 4 pages (English translation provided).

Diagnostica Stago "Staclot® Protein S Additional Information," 1 page (Publication date unknown).

Exner et al. (1978), "A Sensitive Test Demonstrating Lupus Anticoagulant and its Behavioural Patterns," *Br. Haematol.*, 40:143–151.

Faioni et al. (1991), "Low Levels of the Anticoagulant Activity of Protein C in Patients with Chronic Renal Insufficiency: an Inhibitor of Protein C is Present in Uremic Plasma," *Thrombosis and Haemostasis*, 66(4):420–425.

Hoffmann et al. (1978), "Comparison of Reagents for Determining the Activated Partial Thromboplastin Time," *Thromb. Haemost.*, 39:640–645.

Holmberg et al. (1981), "Assessment of Blood Coagulation and General Haemostatis," *Haemostasis and Thrombosis* (Bloom et al. Ed.), Churchill Livingston, London, 768–774.

Hoogendoorn et al. (1991), "$\alpha_2$–Macroglobulin Binds and Inhibits Activated Protein C," *Blood*, 78(9):2283–2290.

Koepke et al. (1986), "Partial Thromboplastin Time–Test Proposed Performance Guidelines," *Thrombosis and Haemostasis*, 55:143–144.

Lottenberg et al. (1981), "Assay of Coagulation Proteases Using Peptide Chromogenic and Fluorogenic Substrates," *Methods in Enzymology* (Colowick et al. Ed.), vol. 8, Protedytic Enzymes Past C (Lorand Ed.), Academic Press, 341–361.

Malm et al. (1988), "Changes In the Plasma Levels of Vitamin K–dependent Proteins C and S of C4b–binding Protein During Pregnancy and Oral Contraception," *Br. Hemat.*, 68:437–443.

Marlar et al. (1982), "Mechanism of Action of Human Activated Protein C, a Thrombin–Dependent Anticoagulant Enzyme," *Blood*, 59(5):1067–1072.

Pollner et al. (1992), "The Activated Partial Thromboplastin Time (APTT)," ECAT Assay Procedures–A Manual of Laboratory Techniques (Jespersen et al. Ed.), Kluwer Academic Publishers, 35–40.

Preda et al. (1990), "A Prothrombin Time–Based Functional Assay of Protein S," *Thromb. Res.*, 60:19–32.

Spaethe (1984), "Härnostase–Physiologie, Pathophysiologie, Diagnostik," 90 (English translation provided).

Stocker et al. (1988), "Practical Application of the Protein C Activator Protac from Agkistrodon ContortrixVenom," *Folia Haematol.*, 115: 260–263.

Stocker et al. (1986), "Protein C Activators in Snake Venoms," *Behring Inst. Mitt.*, 37–47.

Walker, (1990), "Guidelines on The Investigation and Management of Thrombophilia," *J. Clin. Pathol.*, 43:703–709.

Kahn et al. "V. Changes of Molecular Weight Accompanying Activation of Factor V by Thrombin and the Procoagulant Protein of Russell's Viper Venom," *Studies on Blood Coagulation Factor V*, 25–32 (1970).

Yukelson et al. "Procoagulant Activities in Venoms From Central Asian Snakes," *Toxicon*, 29(4/5) 491–502 (1991).

Rosén, et al., "Protein S, an Important Regulatory Protein in Hemostasis," *Protein S—Chromogenix Monograph Series* 21 pages (Nov. 2000, approximate publication date).

Walker, "Protein S and the Regulation of Activated Protein C," *Semin. Thromb. Hemost.* 10(2):131–138 (1984).

Walker, "Regulation of Bovine Activated Protein C By Protein S: The Role of the Cofactor Protein In Species Specificity," *Thromb. Res.* 22:321–327 (1981).

Walker, "Regulation of Activated Protein C by a New Protein," *Bio. Chem.* 255(12):5521–5524 (1980).

Walker, et al., "The Inhibition of Blood Coagulation by Activated Protein C Through the Selective Inactivation of Activated Factor V," *Biochimica et Biophysica Acta* 571:333–342 (1979).

Wiesel, et al., "Screening of Protein S Deficiency Using a Functional Assay in Patients with Venous and Arterial Thrombosis," *Thromb. Res.* 58:461–468 (1990).

Wolf, et al., "Clinical Applications of a Direct Assay of Free Protein S Antigen Using Monoclonal Antibodies. A Study of 59 Cases," *Blood Coag. and Fibrin.* 5:187–192 (1994).

Wolf, et al., "Functional Assay of Protein S in 70 Patients with Congenital and Acquired Disorders," *Blood Coag. and Fibrin.* 2:705–712 (1991).

Diagnostika Stago, "Staclot® Protein C Additional Information" 1 page, (Publication date unknown).

Notification of Transmittal of International Preliminary Examination Report for International Patent Application No. PCT/US01/50338, dated Dec. 19, 2000, 6 pages.

* cited by examiner

PROTEIN S FUNCTIONAL ASSAY AND KIT THEREFOR

This application claims the benefit of Provisional Application No. 60/256,703, filed Dec. 19, 2000.

FIELD OF THE INVENTION

The invention provides a functional protein S assay and methods based on the ability of protein S to prolong the clotting time of plasma in the presence of exogenous Tissue Factor, phospholipids, and activated protein C.

Background of the Invention

Protein S is a vitamin K-dependent anticoagulant protein which circulates in plasma at a concentration of about 25 µg/ml with a half-life of about 2 days. In normal plasma, 60% of protein S binds to C4b-binding protein (C4b-BP) non-covalently in a 1:1 ratio with high affinity. Protein S that is bound to C4b-BP is inactive. The remaining 40% of protein S exists as free protein in plasma and is believed to be the physiologically active anticoagulant form which acts on the cell membrane surface as a cofactor for activated protein C (APC). APC degrades the active forms of procoagulant factors V (FVa) and VIII (FVIIIa) through specific proteolytic cleavage, thereby reducing thrombin generation and prolonging clotting time. Protein S binds to APC and acts as a cofactor and increases the cleavage rate of factors Va and VIIIa. Protein S also exerts a direct inhibitory effect on the prothrombinase complex by binding to factor Xa and to factor Va, and thus impairing prothrombin activation.

Protein S deficiency may be hereditary or acquired. Acquired deficiency may be observed during pregnancy, oral anticoagulant therapy, oral contraceptive use, in liver disease, in newborn infants, as well as in other clinical conditions. Because Protein S is a vitamin K-dependent protein, its concentration decreases during treatment with oral anticoagulants. With a half-life of two days, the rate of decrease for protein S levels is much lower than for protein C and factor VII, which have half-lives of several hours. A representative normal range for total protein S is 70–140%. Considering 25 µg/ml as the mean concentration, this corresponds to a range of 15–35 µg/ml. Protein S levels may be influenced by sex hormones such as estrogens. Premenopausal women have lower values than men and postmenopausal women. Significantly lower mean values of total and free protein S are found in pregnant women (from 25 µg/ml to 15 µg/ml) and women using oral contraceptives (from 25 µg/ml to 18 µg/ml). Acquired and congenital protein S deficiency is associated with an increased risk of thrombosis (e.g., deep vein thrombosis) due to a decrease of blood anticoagulant potential. Hereditary protein S deficiencies include familial thrombophilia.

The current subclassification of protein S deficiency into three types was recommended by the Scientific Standardization Committee of the International Society on Thrombosis and Haemostasis (ISTH) in 1992. Type I is characterized by low levels of total and free protein S with a decrease in functional protein S activity. Type II is characterized by normal levels of total and free protein S with a decrease in functional protein S activity. Type III is characterized by normal levels of total protein S and a low level of free protein S, with a decrease in functional protein S activity.

Antigenic (immunological) assays measure the concentrations of either total or free protein S, depending on the antibody and/or procedure used. Functional assays for protein S measure the biological activity of protein S. Since protein S bound to C4BP does not have anticoagulant activity, it is important to know the concentration of the free protein S that is available to act as a cofactor for APC. Free protein S can be quantitatively determined in several ways, for example, the C4BP-protein S complex may be precipitated with polyethylene glycol and the concentration of free protein S in the supernatant may be determined. Alternatively, free protein S may be directly measured by capturing free protein S with immobilized C4BP (e.g., C4BP bound to wells of a microplate) and quantitating with antibody (Coaliza® Protein S-Free Assay, Chromogenix-Instrumentation Laboratory Company SpA, Milan Italy).

Protein S activity does not always correlate with protein S levels in a plasma sample. For example, a free protein S concentration obtained using an antigenic method correlates well with functional activity for patients with Types I and III but not Type II protein S deficiency for a number of reasons. First, antigenic assays measure both fully carboxylated (active) and non-carboxylated (inactive) forms of free protein S. Second, the functional protein S assays are complicated by the presence of both the free and complexed forms in plasma. Thus, antigenic assays can overestimate the level of functional protein S. For example, an antigenic assay of plasma from patients receiving warfarin will give higher values than those obtained using a functional assay. It is therefore important that both a functional and an antigenic assay be performed to screen patients at risk of thrombotic disease for protein S deficiency (i.e., deficient protein S levels and/or deficient protein S activity).

In some functional protein S activity assays, the effect of free protein S as a cofactor to APC is determined. These assays are predominantly coagulometric and measure the prolongation of the clotting time due to free protein S activity as a consequence of the degradation of FVa and FVIIIa by APC. APC-cofactor methods for free protein S activity have traditionally included the prothrombin time (PT), the activated partial thromboplastin time (APTT) and factor Xa-based methods, described below. In addition, free Protein S also exerts an APC-independent anticogulation activity through direct binding to factor Va, factor Xa and factor VIII. An assay of the APC-independent anticoagulant activity of protein S has been developed in which the clotting time is determined in the presence and absence of a polyclonal protein S antibody.

Protein S functional assays may be based on the prothrombin time (PT). The cofactor activity of protein S is confined to the APC-dependent degradation of factors Va and VIIIa. Originally, a method was developed for characterization of purified protein S, which was later followed by a functional test for determining protein S in plasma. (Walker (1984) Sem. Thromb. Hemost. 10:131–38). Protein S activity is determined by mixing a plasma sample with protein S-deficient plasma. The stimulating effect of protein S on the anticoagulant activity of APC is measured by observing clotting time following the addition of thromboplastin (Tissue Factor) and calcium ions to a plasma sample with and without the addition of exogenous APC or exogenous protein C activator (PCA). PCA may be isolated from snake venom from *Agkistrodon contortrix*, which is known under the proprietary name Protac® C (Pentapharm, Basle, Switzerland). A resolution of 40–50 seconds is obtained between 0 and 100% protein S.

Protein S functional assays alternatively can be based on the prolongation of activated partial thromboplastin time (APTT) due to exogenous APC or exogenous PCA.

The standard APTT reaction begins by adding a surface-activating agent (e.g., Kaolin, silica, ellagic acid) and a phospholipid preparation to a plasma sample, thereby achieving maximum activation of factor XI. Calcium is then added to activate the coagulation cascade and the time for clot formation is determined.

In APC resistance assays (e.g., COATEST and COATEST F), two APTT reactions are performed, one in the presence of APC (or PCA) and the other in its absence. The result can be calculated either as a prolongation of clotting time or as a ratio between the clotting times in the presence or absence of APC (or PCA). The APTT reaction without the addition of APC (or PCA) should be within the normal range of 25–40 seconds.

However, the cut-off value for all assays known to date varies between laboratories, instruments, reagent handling and other preanalytical variables. For this reason, APTT and PT assays typically require that a normal control sample be run in parallel. In such cases, the clotting time and/or clotting time prolongation of the patient sample is compared to that of the normal control sample or samples of known protein S content.

Other protein S assays include FXa-based methods, wherein coagulation is triggered by factor Xa in the presence of calcium ions and phospholipids. Originally, undiluted plasma was used. (Comp (1984) J. Clin. Invest. 74:2082–2088.). This was later replaced by methods to minimize interference by prothrombin levels in the plasma, allowing dilution of test plasma and providing close to 100 seconds resolution between 0 and 100% protein S. (Wiesel et al. (1990) Thromb. Res. 58:461–468.) In one variant of the method, free protein S in the test plasma is first adsorbed on an insolubilized monoclonal protein S antibody. (D'Angelo et al. (1988) J. Clin. Invest. 81:1445–1454). Factor Xa has also been used as a trigger in a system utilizing purified components. Dahlback (1986) J. Biol. Chem. 261:12022–12027).

A prothrombin time method is described in U.S. Pat. No. 5,726,028. The assay uses Thromborel S®, a tissue factor/phospholipid preparation from human placenta and protein C activator. The endogenous protein C in the sample is activated by the protein C activator and forms with protein S active APC/protein S complexes. Clotting is induced by adding calcium ions, and the resulting APC/protein S complexes delay clot formation.

However, this and other assays available generally use crude extracts of tissue factor and phospholipid. In addition, activated protein C, which is also used in the assays is obtained by activating a plasma sample containing protein C with a crude protein C activator, such as snake venom activator, for example. As a consequence of impurities present in these crude reagents, the traditional protein S functional assays suffer from poor reproducibility, low sensitivity and instability.

A need exists, therefore, for a reproducible, sensitive and stable, and functional Protein S assay that, optionally, does not require comparison of the patient results to the results from a normal patient.

BRIEF DESCRIPTION OF THE DRAWINGS

The foregoing and other objects, features and advantages of the present invention, as well as the invention itself, will be more fully understood from the following description of preferred embodiments when read together with the accompanying drawings, in which.

SUMMARY OF THE INVENTION

Figure 1:
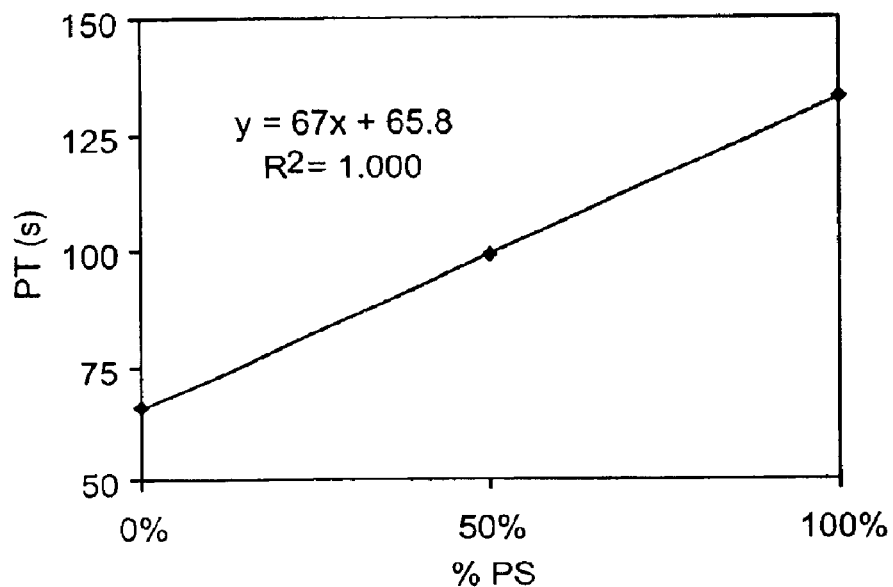
FIG. 1 shows an exemplary calibration curve.

The invention relates generally to a new functional protein S assay and kit that is based on the ability of endogenous protein S to prolong clotting time in response to exogenous PCA or APC. In the assay procedure, a test plasma sample is diluted with protein S-deficient normal plasma, followed by the addition of purified or recombinant tissue factor (pTF or rTF), purified natural or synthetic phospholipid (pPL or sPL) and activated with or without purified or recombinant protein C (pAPC or rAPC) or purified or recombinant protein C activator (pPCA or rPCA) and appropriate salts. The prolongation of clotting time due to exogenous PCA or APC is then determined and is indicative of the protein S activity in the test sample. The prolongation of clotting time obtained for the patient sample may be compared to a standard curve of normal plasma clotting. Insufficient prolongation of clotting time is indicative of protein S deficiency.

The TF may be recombinant (e.g., rabbit or human) or purified (e.g., from rabbit brain or human placenta). The TF is preferably rTF. The TF is preferably re-lipidated with PL prior to adding to the protein S assay reagent.

The PL may be synthetic or purified (e.g., from plant of animal sources). The PL is preferably sPL. In a preferred embodiment, the PL comprises 1,2-dioleoyl-sn-glycero-3-phosphocholine (PC), 1,2-dioleoyl-sn-glycero-3-phospho-L-serine (PS), and 1,2-dioleoyl-sn-glycero-3-phosphoethanolamine (PE). The PC:PS:PE is preferably in a molar ratio of about 3 to about 4 to about 5.

APC is preferably rAPC. If exogenous APC is used, it is preferably derived by activation of exogenous protein C by proteolysis with a suitable enzyme. Preferred enzymes are those which do not activate or otherwise influence any other factors in the clotting system apart from protein C. Particularly preferred is thrombin. Also preferred are protein C activators from the venom of snakes, such as, for example, *Agkistrodon contortrix contortrix, Agkistrodon bilineatus* or *Agkistroron halys halys.*

In embodiments where clotting time is observed chromogenically, for example, a chromogenic substrate for a component of the coagulation cascade influenced by PS-cofactor activity may be added for thrombin to facilitate chromogenic determination.

The PS-deficient plasma, TF and APC are preferably derived from a mammalian source such as, for example, a cow, pig, rabbit or human. The PL is preferably derived from plant or animal sources and is available commercially.

In another aspect, the invention provides a kit for measuring the functional activity of PS having a container containing PS-deficient plasma and one or more containers comprising pTF or rTF; and pPL or sPL; and APC or PCA. The kit may also comprise calibration plasma for preparing a standard curve or a control plasma sample with a known protein S activity.

DESCRIPTION OF PREFERRED EMBODIMENTS

The invention provides a sensitive functional protein S (PS) assay based on the ability of endogenous protein S to prolong the clotting time in response to exogenous APC or PCA in a PT-based assay. Thus, TF, PL, calcium, and PCA or APC are added to an aliquot of a patient's sample, and clotting times are observed. The clotting time is compared to a standard curve of clotting times of plasma samples having known protein S activities. The use of purified or synthetic PL, purified or recombinant TF and purified activated APC allows for optimization of reagent sensitivity, reproducibility and specificity.

The traditional functional protein S assays normally involve the use of TF derived from brain powder extract and crude PL from plant and animal sources. (U.S. Pat. No. 5,726,028). However, endogenous Protein S cannot significantly prolong the clotting time when using these reagents, which are often insensitive to Protein S levels. In the instant invention, the assay reagents are specifically sensitive for measuring protein S activity, and are, therefore, referred to hereinafter collectively as the protein S (PS) reagent.

The contents of a preferred PS reagent and concentration ranges of the reagents are shown in Table 1. The PS reagent contains purified or recombinant Activated Protein C (pAPC or rAPC), purified (pPL) or synthetic PL (sPL) and purified (pTF) or recombinant TF (rTF), to avoid lot to lot variation in activity and sensitivity. In a preferred embodiment the assay contains purified APC, rTF and sPL. The use of sPL and recombinant TF avoids contamination from the source (e.g., brain powder), and provides a much easier and more controllable manufacturing process. The amounts of TF and PL in the PS reagent required by the disclosed assays are less than those required for traditional PT assays.

APC may be generated by activating exogenous or endogenous plasma protein C with snake venom activator (e.g., Protac®), which is time-consuming and which may also result in insufficient or variable activation of APC (e.g., from lot to lot). Alternatively, exogenous protein C may be activated using thrombin as described in Example 4.

The PS reagent of the invention preferably contains purified APC to eliminate the external activation step and to simplify the assay. The use of purified APC (pAPC) ensures that APC levels are constant from assay to assay. Suitable pAPC may be purified from any mammalian source such as, for example, human, bovine, porcine, equine and rabbit.

Alternatively, protein C activator (PCA) is used in the assay to activate endogenous protein C. The concentration of PCA is chosen so that a suitable prolongation of the clotting time in the plasma is generated by the exogenous PCA. A suitable prolongation of the clotting time (as compared with the clotting time in the absence of a PCA) is one which, on the basis of the type of apparatus used, allows significant differences from normal plasmas to be detected. The prolongation time is preferably at least about 25%, 50%, or 75%, particularly preferably at least about 100%, or about 200%.

Tissue Factor (TF; also called thromboplastin) is the protein responsible for triggering blood clotting in PT-based assays. It is an integral membrane protein that must be incorporated into phospholipid vesicles for optimal activity. Recombinant TF (rTF) may be obtained from any mammalian source, such as, for example, human, bovine, porcine, equine. Preferred TF is recombinant rabbit TF, such as that described in U.S. Pat. No. 5,858,724 or 6,100,072, the contents of which are incorporated herein by reference. Recombinant TF may be obtained by in vitro transcription and translation, for example. Alternatively, natural purified TF could be used. TF may be purified according to the method provided in Example 2. In a preferred embodiment, the PS reagent is prepared with rTF that has been re-lipidated with sPL.

Synthetic phospholipid (sPL) may be prepared, e.g., by organic synthesis using standard methods. The sPL of the invention is preferably a mixture of three lipids: 1,2-dioleoyl-sn-glycero-3-phosphocholine (PC), 1,2-dioleoyl-sn-glycero-3-phospho-L-serine (PS), and 1,2-dioleoyl-sn-glycero-3-phosphoethanolamine (PE). In a preferred embodiment, the molar ratio of PC:PS:PE is about 3: about 4: about 5.

sPL used for re-lipidation of TF prior to the protein S assay was prepared by an extrusion method. In this method, PLs are forced or extruded through two different membranes (pore sizes 0.45 µm and 0.1 µm) sequentially and repeatedly forced through a 0.1 µm membrane in order to form lipid vesicles or micelles. Alternatively, PL can be treated by a detergent solubilization process, wherein the PLs are dissolved in detergent to form loose lipid vesicles or micelles. Purified or recombinant TF is then added and becomes incorporated into the vesicles. The detergent is then removed, causing the vesicle to contract or shrink, causing the TF to intercalate between PL molecules. The TF is thereby exposed to the exterior of the vesicle. The protein S assay of the invention involves mixing together test plasma, PS deficient plasma, factor diluent and a PS assay reagent comprising TF, PL and APC or PCA (see, for example, Example 5). Potential analytical interferences are minimized by diluting the test sample about 20-fold with PS-deficient plasma and factor diluent, so that the assay is specific for protein S. The assay results are linear over the range of 5%–150% Protein S activity. The variation of calibration curves is small with <3% coefficient of variation (CV) over a period of 2 weeks. The assay is reproducible, with <3% within-run CV and <5% between-run CV for normal samples, and <5% within-run CV and <8% between-run CV for abnormal samples (<30% PS) (FIG. 1).

Figure 2:
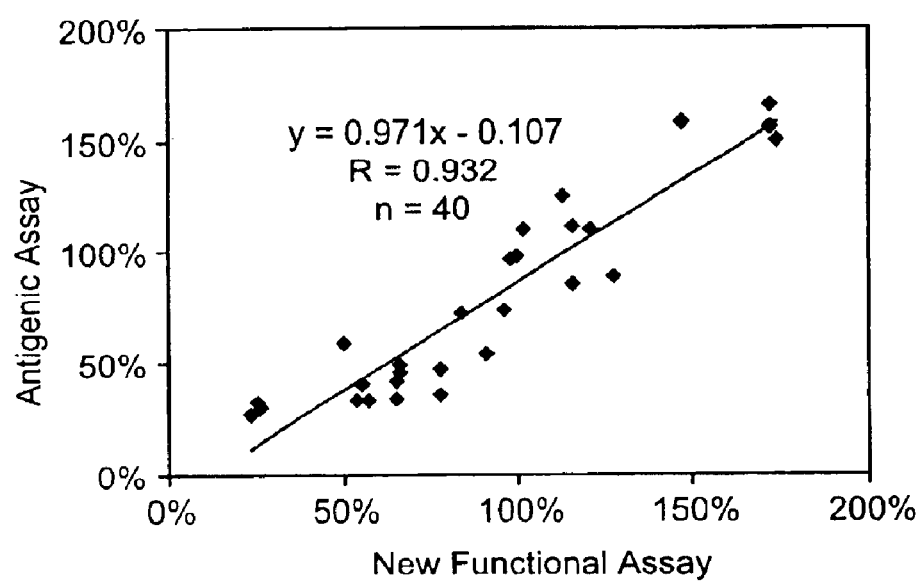
FIG. 2 shows a comparison between PT measurements obtained using the functional assay and the antigenic assay.

The assay specificity was demonstrated by a good correlation between functional PS and free antigenic PS in normal and patient samples (slope=0.971, intercept=0.107, and r=0.932) (FIG. 2). An antigenic assay to determine free PS concentration was performed according to standard methods (e.g., Coaliza). The functional and antigenic protein S assays gave comparable protein S recovery in APC-resistance samples, indicating that APC-resistance does not interfere with the functional assay.

Prolongation of the clotting time may be measured in various ways (e.g., photometrically or chromogenically). When clotting is measured chromogenically, a substrate for a component of the coagulation cascade that is influenced by protein S activity may be added to the assay. An exemplary chromogenic substrate would be a substrate for thrombin (e.g., H-D-Phe-Pip-Arg-pNA-2HCl; MW 625.6; S-2238, Chromogenix).

High sensitivity, specificity, reproducibility and simplicity make this assay suitable for automation on coagulation analyzers (e.g., IL Coagulation or ELECTRA System, Instrumentation Laboratory) according to art known methods, e.g., for screening for congenital and acquired protein S deficiency. In addition, the assay allows the use of calibration curves to determine protein S activity.

EXEMPLIFICATION

Example 1

Preparation of Phospholipids by Extrusion

PLs micelles were prepared by extrusion. In this method, PLs are first suspended in a buffered saline solution to give large, multilamellar vesicles. The vesicle solution, e.g., 0.5–1.0 mls, is then passed through a 0.45 μm polycarbonate membrane and repeatedly passed through a 0.1 μm polycarbonate membrane six times. The result is uniformly sized, unilamellar vesicles, approximately 100 nm in diameter. The extrusion process is performed using, for example a LiposoFast-100 Extruder (Avestin, Inc., Ottawa, Canada). The LiposoFast-100 is a medium pressure extruder that uses compressed gas (e.g., nitrogen) at up to 600 PSI to pressurize the sample cylinder and force the starting material through the membrane. The extruded PL is then added to TF, which attaches to the outside of the lipid vesicle.

Extrusion may be performed according to standard methods or according to the manufacturer's recommendations, e.g., the method of http://tf7.org/methods.html—James H. Morrissey, Dept. of Biochemistry, University of Illinois at Urbana-Champaign, Urbana, Ill. 61801, USA, as follows:

1. Dispense 2.6 μM total phospholipids (PL) in a glass test tube

2. Using a fume hood, dry the PL mixture under a gentle stream of nitrogen or argon. When dry, speed-vac for an additional 60 minutes under high vacuum to remove any residual chloroform.

3. To the dried PL, add 2.6 ml room temperature HBS solution and cover the end of the tube with parafilm. Let sit 1 hr at room temperature.

4. Vortex tube vigorously to completely resuspend the PL. The result should be a milky, uniform suspension. You can aid the process of resuspension by freezing and thawing the suspension multiple times (as many as ten times).

5. Load 0.5 ml of the lipid suspension into one of the two glass syringes (containing a 0.45 μm filter) of the Lioposofast machine and attach it to the Luer lock on one side of the device. Close the other (empty) syringe and attach it to the Luer lock on the opposite side of the device.

7. Press the loaded syringe to pass its entire contents through the filter and into the opposing syringe. Change the 0.45 μm to a 0.1 μm Repeat this process alternately with the two syringes for a total of at least 7 passes. It is essential that you always use an odd number of passes, so that the final product will end up in what was originally the empty syringe. This will ensure that none of the starting multilamellar vesicles will contaminate the final product.

8. Remove the final product and repeat steps 6 and 7 for the remaining, unprocessed phospholipid suspension, until all of the suspension has been processed.

9. Store the final product at 4° C. The result is a uniform suspension of unilamellar vesicles (about 100 nm in diameter) containing a total of 1 mM phospholipid in HBS.

Example 2

Purification of TF from Cell Lysates

Tissue factor (TF) is purified from cell lysates using the following method. Cells producing TF are washed with TBS and resuspended to $2 \times 10^7$/ml in TBS containing 0.25% Triton-X100, 10 μg/ml soybean trypsin inhibitor, and 1 mM EDTA. After incubation for 30 min at 4° C., the cellular debris is removed by centrifuging for 20 min at about 5000×g at 4° C. The clarified lysate is diluted 2.5-fold with TBS to reduce the Triton concentration to 0.1% and passed through an immunoaffinity resin containing a covalently coupled monoclonal antibody directed against TF. The resin bed is washed with 2 to 3 bed volumes of TBS+0.1% Triton-X100, 2 to 3 volumes 20 mM Tris, pH 7.5, 0.5 M NaCl, 0.1% Triton-X100, and finally 2 to 3 bed volumes 0.5 M NaCl, 0.1% Triton-X100. The bound protein is eluted from the resin with 0.1 M glycine, pH 2.5, 0.1% Triton-X100. Fractions collected after the buffer was changed to glycine are neutralized immediately with an appropriate volume of 1 M Tris, pH 8. TF is found in those fractions immediately surrounding the point where the pH of the column effluent changes. The fractions containing TF are pooled, dialyzed against 20 mM Tris, pH 8, 0.1% Triton-X100, and concentrated by binding the TF to a small bed volume DEAE Trisacryl column (IBF Biotechniques, Columbia, Md.). The Triton-X100 is replaced with CHAPS (Calbiochem.) by washing the resin bed with at least 10 bed volumes of 20 mM Tris, pH 8 containing 10 mM CHAPS. The TF is eluted with a single step of 0.5 M NaCl in 20 mM Tris, pH 8, 10 mM CHAPS.

Example 3

Re-lipidation of Tissue Factor

A preferred re-lipidation process is as follows: 66 g of sPL is reconstituted with 4.4 ml of 100 mM CHAPS in buffer. The sPL was mixed at 30–37° C. until completely dissolved. The PL was transferred into a jacketed, PVDF-coated vessel and the lipid container rinsed with 2×volume (400 ml) buffer. 100 ml 20 mM CHAPS/BGG was added to the PVDF-coated vessel and mixed at 200–400 RPM for 5–10 min., avoiding excess foaming. Recombinant TF was quick thawed and was added to the PL. The remaining buffer was added to the TF/PL mixture. The TF/PL mixture was incubated for 55–65 min. at 27–33° C. with an overhead mixer at 200–400 RPM. XAD-6 resin was washed with buffer and aliquoted into 6 aliquots. One aliquot of the resin was vacuum-filtered and added to the TF/PL mixture. The TF/PL mixture was incubated with mixing using an overhead mixture at 200–400 RPM for 2 hours +/−15 min. at 27–33° C. Additional aliquots of resin were added to the TF/PL mixture. After the addition of the $4^{th}$ aliquot, the TF/PL mixture remained mixing overnight at 27–33° C. At day 3, the remaining aliquots of resin were added and the TF/PL mixture was filtered through a series of 250 μM NYTEX Mesh, 2–10 and 0.22 μM filters and mixed for 15 min. 4 L of dilution buffer was added to 1 L undiluted TF/PL mixture and mixed for 15 min.

Example 3

Tissue Factor Relipidation Using Detergent

This technique for incorporating TF into PL vesicles uses the dialyzable, non-ionic detergent, n-octyl-beta-D-glucopyranoside (octylglucoside) (Calbiochem Corp., La Jolla, Calif.). (http://tf7.org/methods.html; Neuenschwander et al. (1993) J. Biol. Chem. 268:21489–21492) (see also U.S. Pat. No. 6,203,816, the contents of which are incorporated herein by reference).

In this method, PLs and TF are both dissolved in octylglucoside, forming mixed micelles. Since octylglucoside has a high critical micelle concentration (CMC=20 to 25 mM), it can readily be removed from solutions by dialysis. As the octylglucoside dialyses out, the phospholipids organize into unilamellar vesicles. TF becomes embedded in these vesicles by virtue of its single membrane-spanning domain, located near the C-terminus of the protein. Typically, about 50 to 80% of the TF molecules face outward in these vesicles. The remaining TF molecules face inward and are therefore unable to interact with factor VII/VIIa. (Neuenschwander et al. (1993) J. Biol. Chem. 268:21489–21492). To obtain relipidated TF that is not contaminated with detergent, it is preferable to use TF stock solutions that contain a dialyzable detergent like CHAPS or octylglucoside, rather than Triton. PLs in aqueous solution are subject to oxidation. For this reason, once TF has been relipidated it should typically be used within about 2 or 3 weeks. (For some applications, older TF preparations can still be used with good results. Be aware, though, that such preparations may contain oxidized phospholipids.)

For most applications, TF activity is maximal when vesicles contain 20 mol % phosphatidylserine or less, so there is normally no reason to exceed this level. Note that soluble tissue factor (sTF) cannot be incorporated into phospholipids; in which the membrane spanning domain is intact should be used. Blank vesicles can be made simply by leaving out the TF in the protocol.

Preparation of Phospholipid Solution in Octylglucoside

1. For each sample, dispense 2.6 $\mu$M total PLs in a glass test tube, using the desired polar ratio of PL (e.g., 30% PC, 40% PS, 50% PE) (Avanti Polar Lipid, Alabaster, Ala.).
2. Dry the PL mixture under a gentle stream of argon or nitrogen. If possible, set the tube at an angle so the PLs form a thin film on the side of the tube.
3. When the tube appears dry, speed-vac for an additional 60 minutes under high vacuum to ensure that residual chloroform is removed.
4. To the tube of dried-down PLs, add 400 $\mu$l freshly prepared OG/HBS solution (100 mM n-octyl-beta-D-glucopyranoside in HBS (100 mM NaCl, 20 mM Hepes/NaOH buffer, pH 7.5, 0.02% (w/v) sodium azide (RT))). Vortex vigorously to completely dissolve the dried-down PLs.

Relipidation Procedure

5. To the tube containing 400 $\mu$l of PL/octylglucoside solution, add the desired amount of membrane TF (preferably, dissolved in CHAPS or octylglucoside) and enough HBSA (HBS with 0.1% (w/v) bovine serum albumin) to make the final volume 1 ml. A typical molar ratio of PL to TF is 8700:1, ratios as high as 50,000:1 and as low as 3,000:1 may be used. The final volume will be 1 ml.
6. Mix well and incubate the sample for 30 min at room temperature (RT).
7. Dialyze the sample at RT against three changes of HBS (24 hr each, for a total of 72 hr). Store the final product at 4° C.

The final product is about 1 ml of relipidated TF containing approximately 2.6 mM phospholipid. Because the recovery from dialysis may not be 100%, these amounts are only approximate. Precise concentrations of available TF and total PL can be determined by performing an analysis of exposed TF (titrate with factor VIIa by measuring the TF-induced increase in VIIa amidolytic activity), and an analysis of PL content. (Neuenschwander et al.).

Example 4

Preparation of Activated Protein C

In a preferred embodiment, APC is derived by activation of protein C with thrombin according to standard methods. For example, a frozen protein C fraction from human placenta (Pharmacia UpJohn) is filtered and affinity purified using an Affigel column to which HPC-4 monoclonal antibody (specific for human protein C) (Instrumentation Laboratory Company) is bound. The affinity purified PC is eluted from the Affigel HPC-4 column and is ultrafiltered again. SP Sephadex C-50 purified thrombin is added to the purified PC to activate the PC (APC). The APC is passed through a SP-Sephadex C-50 to remove the thrombin. $CaCl_2$ and BSA are added to the eluate containing purified APC.

Example 5

The Protein S Assay

Human plasma samples were tested for Protein S activity as compared to a standard curve. The assay was performed as follows: Nine parts freshly drawn venous blood was collected into one part trisodium citrate and red cells removed by standard methods. 4 $\mu$l of the blood plasma sample is mixed with 25 $\mu$l of PS deficient plasma (0.1 ml human plasma which has been artificially depleted of protein S), lyophilized and resuspended in 1.0 ml $H_2O$), 51 $\mu$l of factor diluent (0.85% sodium chloride, 0.1% sodium azide and 80 $\mu$l of PS assay reagent (15 mM HEPES, free acid, 18 mM HEPES sodium, 5 g/l bovine serum albumin, 140 mM sodium chloride, 10 mM calcium chloride, 0.0067% sodium omadine, 50 $\mu$M ciprofloxacin, 0.0667% polybrene, 300 ng/l recombinant rabbit tissue factor, 12.5 $\mu$M synthetic phospholipid (PC/PS/PE 3:4:5, e.g., 9.66 $\mu$M PC, 12.9 $\mu$M PS, 16.1 $\mu$M PE), 4 mg/l activated human protein C; pH7.5) and the clotting time measured using a coagulation instrument or a spectrophotometer.

Any of a number of coagulation instruments may be used to perform the test and measure clotting time, (e.g., the ACL, ACL Futura, or ELECTRA; Instrumentation Laboratory Company, Lexington, Mass.). Depending on the type of machine used, a calibration curve may be generated and used for measuring a number of samples before another calibration curve must be generated. The instrument is programmed to make a calibration curve from various mixtures of calibration plasma (plasma in which the coagulation factor levels are known and which contains about 100% protein S) and protein S-deficient plasma (containing about 0% protein S). The two solutions act as the two end points of the curve and intermediate points on the curve are generated by mixing different relative amounts of the two plasmas and measuring their clotting time. For example, serial dilutions of calibration plasma with protein S-deficient plasma may generate plasma samples with about 10%, about 20%, about 30%, about 40%, about 50%, about 60%, about 70%, about 80% or about 90% protein S activity. Once the calibration curve samples have been measured, the clotting times vs. protein S concentration is graphed. The clotting times of test samples are then measured and read against the curve to obtain protein S activity. As a quality control measure, protein S control plasma with a pre-determined protein S activity is run along side the samples to ensure the assay is performing accurately.

Data analysis is performed according to instrumentation specifications. For example, using an ACL, ACL Futura or ELECTRA instrument, results are reported automatically by the instrument as % activity. Each laboratory must establish there own normal range. For an ACL Futura or ELECTRA instrument, once a calibration run is complete and a standard curve is generated, the instrument will store the calibration for future patient runs.

The optimized concentrations and suitable concentration ranges of the PS reagent ingredients are shown in Table I. To avoid possible influence of Factor V Leiden mutation (APC-R) on the actual values, patient samples with results outside the normal range should be manually diluted 1:2 with Protein S deficient plasma and re-assayed. The result is then multiplied by 2.

An exemplary calibration or standard curve is shown in FIG. 1. A patient's plasma sample was tested and a functional protein S level was read from the calibration curve by comparing the coagulation time of the patient sample to the value on the curve. The prolongation of the clotting time was proportional to the protein S activity in the test sample.

A comparison of the performance of three coagulation instruments is shown in Table II. In this experiment, normal control plasma was run against protein S control plasma and the % protein S determined both within and between runs. Correlation between the ACL, ACL Futura and ELECTRA systems showed a slope of 1.01, 1.02 and 1.03, respectively. All three machines achieved linearity for PS activity between 10% and 150%. These results demonstrate the precision and reproduciability of the assay.

TABLE II

|  | Means (% PS) | CV % (Within run) | CV % (Between run) |
|---|---|---|---|
| ACL |  |  |  |
| Normal Control | 95.0 | 2.6 | 3.1 |
| Protein S Control | 32.3 | 2.5 | 3.8 |
| ACL Futura |  |  |  |
| Normal Control | 93.8 | 3.6 | 4.5 |
| Protein S Control | 31.1 | 4.1 | 7.3 |
| ELECTRA |  |  |  |
| Normal Control | 90.9 | 1.4 | 4.1 |
| Protein S Control | 27.2 | 2.1 | 6.4 |

| Correlation: System | slope | intercept | r | Reference method |
|---|---|---|---|---|
| ACL | 1.01 | −5.883 | 0.982 | IL Clotting Protein S on ACL |
| ACL Futura | 1.02 | −4.890 | 0.984 | IL Clotting Protein S on ACL |
| ELECTRA | 1.01 | −6.614 | 0.986 | IL Clotting Protein S on ACL |

| Linearity: System | |
|---|---|
| ACL, ACL Futura and ELECTRA | 10–150 (% PS activity) |

The precision and correlation results were obtained using specific lots of reagents and controls.

TABLE I

Optimal Concentrations and Concentration Ranges of Assay Reagents

| Materials | Optimized Concentration | Concentration Range |
|---|---|---|
| HEPES Free Acid | 15 mM | 10–20 mM |
| HEPES Sodium Salt | 18 mM | 10–25 mM |
| Sodium Chloride | 140 mM | 130–150 mM |
| Calcium Chloride | 10 mM | 8–12 mM |
| Sodium Omadine | 0.0067% | 0.0040–0.0100% |
| Ciprofloxacin | 50 µM | 30–100 µM |
| Polybrene | 0.667% | 0.600–1.00% |
| BSA | .5% | 3–7.5 g/L |
| sPL | 12.5 µM | 10.0–15.0 µM |
| APC | 4 mg/L | 3–5 mg/L |
| rTF | 0.3 mg/L | 0.8–1.2 µg/L |
| pH | 7.5 | 7.45~7.65 |

Table III shows a comparison of the methods of the invention to immunoglobulin assays for plasma samples from patients with various diseases. Column 2 shows the protein S assay of the invention performed on an ACL3000 instrument. Column 3 shows instant protein S assay of the invention performed on a Futura instrument. Column 4 shows a protein S assay (utilizing bovine TF) performed on an ACL3000 instrument. Column 5 shows the results using a IL Test™ Free Protein S kit (Latex-immunological). Column 6 shows the results using a Coaliza® test kit. Column 7 shows the difference between the values obtained in Column 3 minus Column 2. Column 8 shows the differences in values obtained in Column 5 minus Column 2. Column 10 shows the difference between the values obtained for Column 6 minus Column 2. Column 11 shows the difference between the values in Column 6 minus Column 5.

TABLE III

Comparison of the Protein S assay to the Bovine TF, FPS (Latex) and ELISA assays on various coagulation machines.

| | Disease state | ProS (ACL3000) | ProS (Futura) | Bov (ACL3000) | FPS (Latex) | ELISA | ProS(Futura) Minus New (ACL3000) | Bovine Minus New (ACL3000) | rPS(Latex) Minus New (ACL3000) | ELISA Minus New (ACL3000) | ELISA % Minus FPS (Latex) |
|---|---|---|---|---|---|---|---|---|---|---|---|
| 1 | PS Type II 1 (11) | 26% | 25% | 30% | 29% | 33% | -1% | 4% | 3% | 7% | 4% |
| 2 | PS Type11 3 | 23% | 23% | 30% | 27% | 26% | 0% | 7% | 4% | 3% | -1% |
| 3 | PS def 6 | 25% | 24% | 36% | 32% | 32% | -1% | 11% | 7% | 7% | 0% |
| 4 | PS/PC 10 | 65% | 67% | 68% | 42% | 50% | 2% | 3% | -23% | -15% | 8% |
| 5 | PS/PC 9 | 78% | 65% | 73% | 47% | 55% | -13% | -5% | -31% | -23% | 8% |
| 6 | PS/PC 7 | 57% | 48% | 50% | 33% | 36% | -9% | -7% | -24% | -21% | 3% |
| 7 | PS/PC 8 | 55% | 51% | 60% | 41% | 46% | -4% | 5% | -14% | -10% | 5% |
| 8 | Liver 1 | 66% | 61% | 78% | 50% | 62% | -5% | 12% | -16% | -4% | 12% |
| 9 | Liver 2 | 121% | 111% | 117% | 110% | 104% | -10% | -4% | -11% | -17% | -6% |
| 10 | OAC 12 | 66% | 55% | 65% | 46% | 52% | -11% | -1% | -20% | -14% | 6% |
| 11 | Heprin 12 | 96% | 88% | 96% | 74% | 85% | -8% | 0% | -22% | -11% | 11% |
| 12 | Heprin 13 | 128% | 116% | 127% | 89% | 97% | -12% | -1% | -39% | -31% | 7% |
| 13 | OAC 11 | 78% | 62% | 83% | 36% | 40% | -16% | 5% | -43% | -38% | 5% |
| 14 | OAC 13 | 54% | 45% | 51% | 33% | 33% | -9% | -3% | -21% | -21% | 0% |
| 15 | OAC 14 | 65% | 53% | 61% | 33% | 37% | -12% | -4% | -32% | -29% | 3% |
| 16 | OAC 15 | 91% | 78% | 86% | 54% | 63% | -13% | -5% | -37% | -29% | 9% |
| 17 | PS high 7 | 174% | 162% | 172% | 151% | 168% | -12% | -2% | -23% | -6% | 17% |
| 19 | PS high 6 | 172% | 172% | 174% | 156% | 172% | 0% | 2% | -16% | 0% | 16% |
| 20 | PS high 10 | 172% | 160% | 178% | 166% | 154% | -12% | 6% | -6% | -18% | -12% |
| 22 | PS high 9 | 147% | 150% | 142% | 158% | 162% | 3% | -5% | 11% | 15% | 4% |
| 24 | GK N.P.1 | 84% | 72% | 79% | 73% | 80% | -12% | -5% | -12% | -4% | 8% |
| 25 | GK N.P.2 | 50% | 43% | 58% | 59% | 60% | -7% | 8% | 9% | 10% | 1% |
| 26 | GK N.P.3 | 116% | 93% | 107% | 86% | 85% | -23% | -9% | -30% | -31% | -1% |
| 27 | APCR 241 | 102% | 89% | 100% | 110% | 110% | -13% | -2% | 8% | 8% | 0% |
| 30 | APCR 24132 | 100% | 95% | 96% | 98% | 109% | -5% | -4% | -2% | 9% | 11% |
| 34 | APCR 23974 | 98% | 85% | 96% | 97% | 106% | -13% | -2% | -1% | 8% | 9% |
| 37 | APCR 23976 | 113% | 96% | 112% | 125% | 122% | -17% | -1% | 12% | 9% | -4% |
| 40 | APCR 23969 | 116% | 99% | 118% | 112% | 125% | -17% | 2% | -4% | 9% | 14% |

Equivalents

The invention may be embodied in other specific forms without departing from the spirit or essential characteristics thereof. The foregoing embodiments are therefore to be considered in all respects illustrative rather than limiting of the invention described herein.

We claim:

1. A method for measuring protein S activity in a test plasma sample comprising:

(a) mixing a sample of test plasma with protein S deficient plasma, at least one recombinant tissue factor selected from the group consisting of recombinant rabbit, recombinant porcine, recombinant equine and recombinant human tissue factors, purified or synthetic phospholipids comprising phosphocholine, phosphoserine and phosphoethanolamine, activated protein C, calcium ion, and measuring a clotting time of the sample, (b) comparing the measurement in (a) to a standard curve derived from clotting times of plasma samples having a range of known protein S activities.

2. The method of claim 1 wherein the phospholipids comprise 1,2-dioleoyl-sn-glycero-3-phosphocholine, 1,2-dioleoyl-sn-glycero-3-phospho-L-serine and 1,2-dioleoyl-sn-glycero-3-phosphoethanolamine.

3. The method of claim 2 wherein the molar ratio of 1,2-dioleoyl-sn-glycero-3-phosphocholine, 1,2-dioleoyl-sn-glycero-3-phospho-L-serine and 1,2-dioleoyl-sn-glycero-3-phosphoethanolamine is about 3 to about 4 to about 5.

4. The method of claim 1 wherein the activated protein C has been activated by thrombin.

5. The method of claim 1 wherein the activated protein C has been activated by snake venom.

6. The method of claim 1 wherein the activated protein C comprises recombinant protein C.

7. The method of claim 1 wherein one or more of the protein S deficient plasma, recombinant tissue factor and activated protein C is derived from a mammalian source selected from the group consisting of a cow, a pig and a rabbit.

8. The method of claim 1 wherein one or more of the protein S deficient plasma, recombinant tissue factor and activated protein C is derived from a human.

9. The method of claim 1 wherein the measuring step is chromogenic.

10. The method of claim 1 wherein the measuring step is spectrophotometric.

11. The method of claim 1 wherein the at least one recombinant tissue factor comprises a recombinant rabbit tissue factor.

12. The method of claim 1 wherein the at least one recombinant tissue factor comprises a recombinant porcine tissue factor.

13. The method of claim 1 wherein the at least one recombinant tissue factor comprises a recombinant equine tissue factor.

14. The method of claim 1 wherein the at least one recombinant tissue factor comprises a recombinant human tissue factor.

15. The method of claim 1 wherein the at least one recombinant tissue factor is purified from mammalian cells.

16. A kit for measuring the functional activity of protein S in a plasma sample, said kit comprising one or more containers containing protein S deficient plasma, at least one recombinant tissue factor selected from the group consisting of recombinant rabbit, recombinant porcine, recombinant equine and recombinant human tissue factors, purified or synthetic phospholipids comprising phosphocholine, phosphoserine and phosphoethanolamine, calcium ion and activated protein C.

17. The kit of claim 16 further comprising calibration plasma comprising about 100% percent protein S activity for preparing a standard curve.

18. The kit of claim 16 further comprising normal control plasma comprising between about 40–50% protein S activity.

19. The kit of claim 16 wherein the phospholipids comprise 1,2-dioleoyl-sn-glycero-3-phosphocholine, 1,2-dioleoyl-sn-glycero-3-phospho-L-serine and 1,2-dioleoyl-sn-glycero-3-phosphoethanolamine.

20. The kit of claim 19 wherein the molar ratio of 1,2-dioleoyl-sn-glycero-3-phosphocholine, 1,2-dioleoyl-sn-glycero-3-phospho-L-serine and 1,2-dioleoyl-sn-glycero-3-phosphoethanolamine is about 3 to about 4 to about 5.

21. The kit of claim 16 wherein the at least one recombinant tissue factor comprises a recombinant rabbit tissue factor.

22. The kit of claim 16 wherein the at least one recombinant tissue factor comprises a recombinant porcine tissue factor.

23. The kit of claim 16 wherein the at least one recombinant tissue factor comprises a recombinant equine tissue factor.

24. The kit of claim 16 wherein the at least one recombinant tissue factor comprises a recombinant human tissue factor.

25. The kit of claim 16 wherein the at least one recombinant tissue factor is purified from mammalian cells.

26. The kit of claim 16 further comprising a chromogenic substrate.

* * * * *

UNITED STATES PATENT AND TRADEMARK OFFICE
CERTIFICATE OF CORRECTION

| | | |
|---|---|---|
| PATENT NO. | : 6,855,509 B2 | Page 1 of 1 |
| APPLICATION NO. | : 10/029406 | |
| DATED | : February 15, 2005 | |
| INVENTOR(S) | : Dai et al. | |

It is certified that error appears in the above-identified patent and that said Letters Patent is hereby corrected as shown below:

At column 16, line 24, directly after claim 26, the following claim should be inserted:

--27. The kit of claim 16 wherein the activated protein C comprises recombinant protein C.--

Signed and Sealed this

Seventh Day of November, 2006

JON W. DUDAS
*Director of the United States Patent and Trademark Office*